(12) United States Patent
Nomura et al.

(10) Patent No.: US 6,499,335 B2
(45) Date of Patent: Dec. 31, 2002

(54) GAS SENSOR

(75) Inventors: Tohru Nomura, Osaka (JP); Hideki Okoshi, Osaka (JP); Tomoko Yoshimura, Osaka (JP)

(73) Assignee: Figaro Engineering, Inc., Osaka (JP)

( * ) Notice: Subject to any disclaimer, the term of this patent is extended or adjusted under 35 U.S.C. 154(b) by 44 days.

(21) Appl. No.: 09/734,546

(22) Filed: Dec. 13, 2000

(65) Prior Publication Data

US 2001/0003916 A1 Jun. 21, 2001

(30) Foreign Application Priority Data

Dec. 16, 1999 (JP) .......................... 11-356868

(51) Int. Cl.[7] .......................... G01N 7/00; G01N 19/10; G01N 27/12
(52) U.S. Cl. ........................ 73/31.06; 73/23.2
(58) Field of Search ................ 73/23.2, 23.31, 73/31.05, 31.06

(56) References Cited

U.S. PATENT DOCUMENTS 3,676,820 A * 7/1972 Taguchi .................. 73/31.06
5,457,333 A * 10/1995 Fukui .................... 73/31.06

FOREIGN PATENT DOCUMENTS

JP 5-45318 * 2/1993 ................ 73/31.06
JP 11-142356 5/1999 ................ 73/31.06

* cited by examiner

*Primary Examiner*—Daniel S. Larkin
(74) *Attorney, Agent, or Firm*—Arent Fox Kintner Plotkin & Kahn, PLLC

(57) ABSTRACT

A central electrode 12 is arranged in a coiled heater electrode 10. They are buried in a $SnO_2$-based inner area 6, and the entirety is covered by a filter 8. The volume of the inner area 6 is set at from $1\times10^{-3}$ $mm^3$ to $16\times10^{-3}$ $mm^3$, the total volume of the bead 4 is set at from $15\times10^{-3}$ $mm^3$ to $70\times10^{-3}$ $mm^3$, and the ratio of the total volume of the bead 4 to the volume of the inner area 6 is set at from four to twenty to bring the sensor resistance in CO and that in methane closer to each other and increase the selectivity from hydrogen.

6 Claims, 8 Drawing Sheets

Inner Volume and Sensor Characteristics at High Temp.

F I G. 5
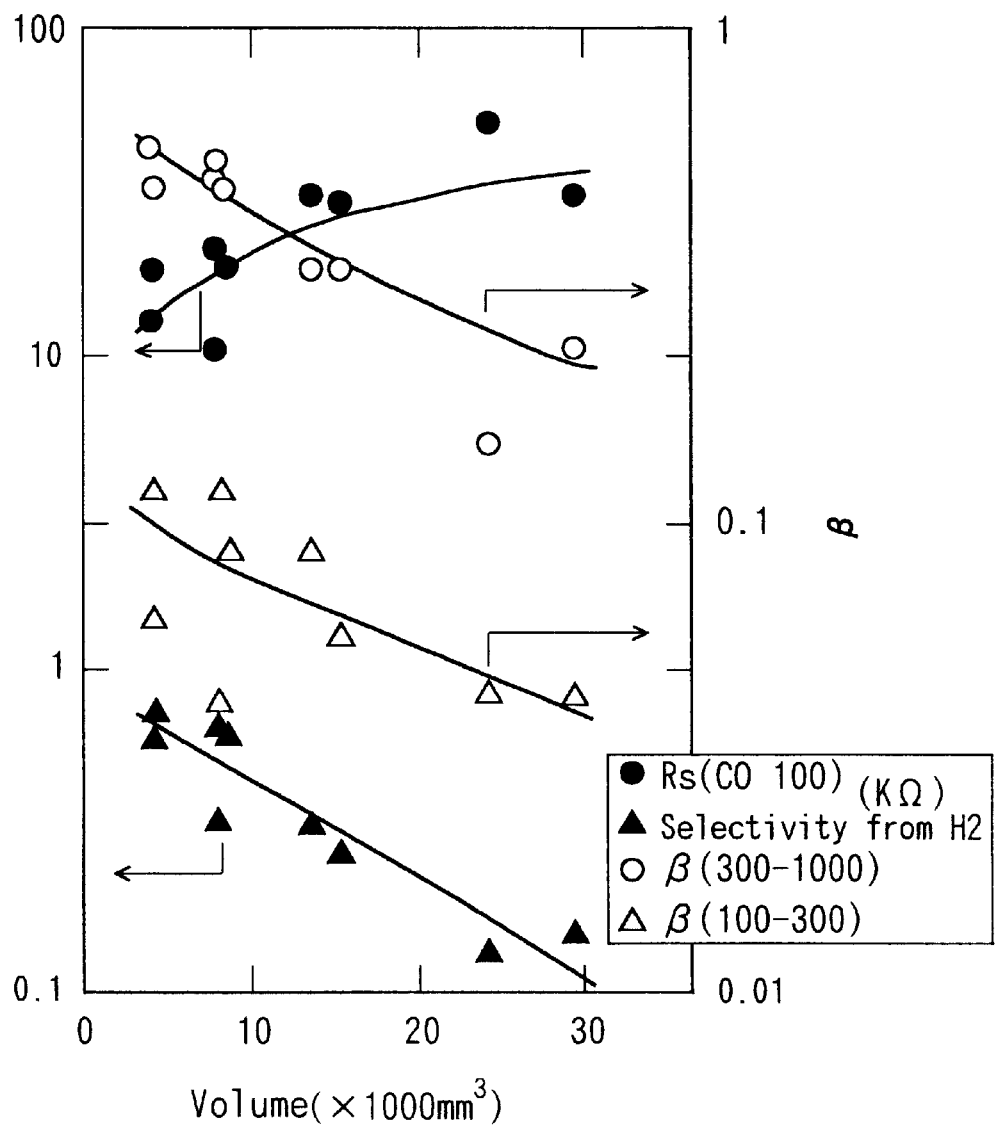
Inner Volume and Sensor Characteristics at Low Temp.

Total Volume and Sensor Characteristics at High Temp.

Total Volume and Sensor Characteristics at Low Temp.

Total Volume/Inner Volume and Sensor Characteristics at High Temp.

Total Voume/Inner Volume and Sensor Characteristics at Low Temp.

GAS SENSOR

FIELD OF THE INVENTION

The present invention relates to improvement in a gas sensor having a coiled heater electrode.

PRIOR ART

A gas sensor is known wherein the surface of a metal oxide semiconductor having a coiled heater electrode is covered by a filter (for example, Japanese Patent Opening Hei 11-142356). Such a gas sensor is used, for example, by subjecting the gas sensor to periodical temperature changes, to detect CO at low temperature and a combustible gas, such as methane, at high temperature. As interfering gases, such as alcohol, can be easily removed with activated carbon filter or the like, the main interfering gas is hydrogen when CO is to be detected and when a combustible gas is to be detected. The resistance of the sensor in CO is generally higher than that of the sensor in a combustible gas, and this poses a problem in designing a detection circuit.

SUMMARY OF THE INVENTION

The objects of the present invention are
1) to bring the sensor resistance in CO and that in a combustible gas close to each other,
2) to improve the selectivity from hydrogen towards CO and combustible gases,
3) to increase the concentration dependency in the combustible gases, and
4) to decrease the concentration dependency in CO of low concentrations.

The present invention is a gas sensor wherein an inner area of $SnO_2$ is provided to cover a coiled heater electrode and the inner area is covered by a filter, said gas sensor being characterized in
that the volume of the inner area is from $1\times10^{-3}$ mm$^3$ to $16\times10^{-3}$ mm$^3$
and that the ratio of the total volume of the inner area and the filter to the volume of the inner area is from four to twenty.

Preferably, the volume of the inner area is from $3\times10^{-3}$ mm$^3$ to $10\times10^{-3}$ mm$^3$, the ratio of the total volume of the inner area and the filter to the volume of the inner area is from four to fifteen, and the total volume of the inner area and the filter is from $15\times10^{-3}$ mm$^3$ to $70\times10^{-3}$ mm$^3$.

More preferably, the volume of the inner area is from $4\times10^{-3}$ mm$^3$ to $10\times10^{-3}$ mm$^3$, the ration of the total volume of the inner area and the filter to the volume of the inner area is from five to fifteen, and the total volume of the inner area and the filter is from $30\times10^{-3}$ mm$^3$ to $60\times10^{-3}$ mm$^3$.

Preferably, a central electrode is provided at the center of said heater electrode.

Preferably, both the filter and the inner area contain $SnO_2$, the filter contains an aggregate, such as alumina, silica and zeolite, and the content of the aggregate in the filter is equal to or higher than that in the inner area. The content of the aggregate in the inner area may be zero.

Preferably, the concentration of a precious metal catalyst such as Pd and Pt, in the filter is lower than that in the inner area, and in the extreme case the filter may not contain any precious metal catalyst.

The present inventor examined how three factors, namely, the volume of the inner area, the total volume of the inner area and the filter, and the ratio of the total volume to the volume of the inner area, influence the characteristics of the gas sensor. The objectives were to bring the sensor resistance in CO and that in a combustible gas close to each other, to increase the selectivity from hydrogen towards CO and combustible gases, to increase the concentration dependency in combustible gases, and to decrease the concentration dependency in CO of low concentration (for example, from 100 ppm to 300 ppm). The concentration dependency in CO of low concentration is generally too high. For example, the resistance in CO of 300 ppm is 1/20 or lower of the resistance in CO of 100 ppm, and as the concentration dependency is too high, it is hard to design a driving and detecting circuit.

We have found that the volume of the inner area and the ratio of the total volume to the inner area influence the sensor characteristics at low temperature (characteristics for CO detection), and that the total volume influences the sensor characteristics for combustible gas detection. As for the inner volume and the volume ratio, when the volume of the inner area is small and the volume ratio is high, the resistance in CO is low and is closer to the resistance in the combustible gases, and the selectivity from hydrogen increases and the concentration dependency on CO at low concentrations decreases. On the basis of the values of these factors of the gas sensors produced on a trial basis, the volume of the inner area was set to be from $1\times10^{-3}$ mm$^3$ to $16\times10^{-3}$ mm$^3$, preferably from $3\times10^{-3}$ mm$^3$ to $10\times10^{-3}$ mm$^3$, and more preferably from $4\times10^{-3}$ mm$^3$ to $10\times10^{-3}$ mm$^3$. Similarly, the ratio of the total volume to the volume of the inner area was set to be from four to twenty, preferably from four to fifteen, and more preferably from five to fifteen.

The sensor characteristics in the combustible gases depend, as describe above, on the total volume. It was found that when the total volume is reduced, the sensor resistance in the combustible gas will decrease, but the selectivity from hydrogen will increase, the concentration dependency will increase, and at the same time the sensitivity to the combustible gases will increase. On the basis of these findings, the total volume was set to be from $15\times10^{-3}$ mm$^3$ to $70\times10^{-3}$ mm$^3$, and preferably from $30\times10^{-3}$ mm$^3$ to $60\times10^{-3}$ mm$^{-3}$.

BRIEF DESCRIPTION OF THE DRAWINGS

FIG. 5 is a characteristic diagram showing the relationship between the inner volume and the sensor characteristics at low temperature of the gas sensor.

EMBODIMENT

Figure 1:
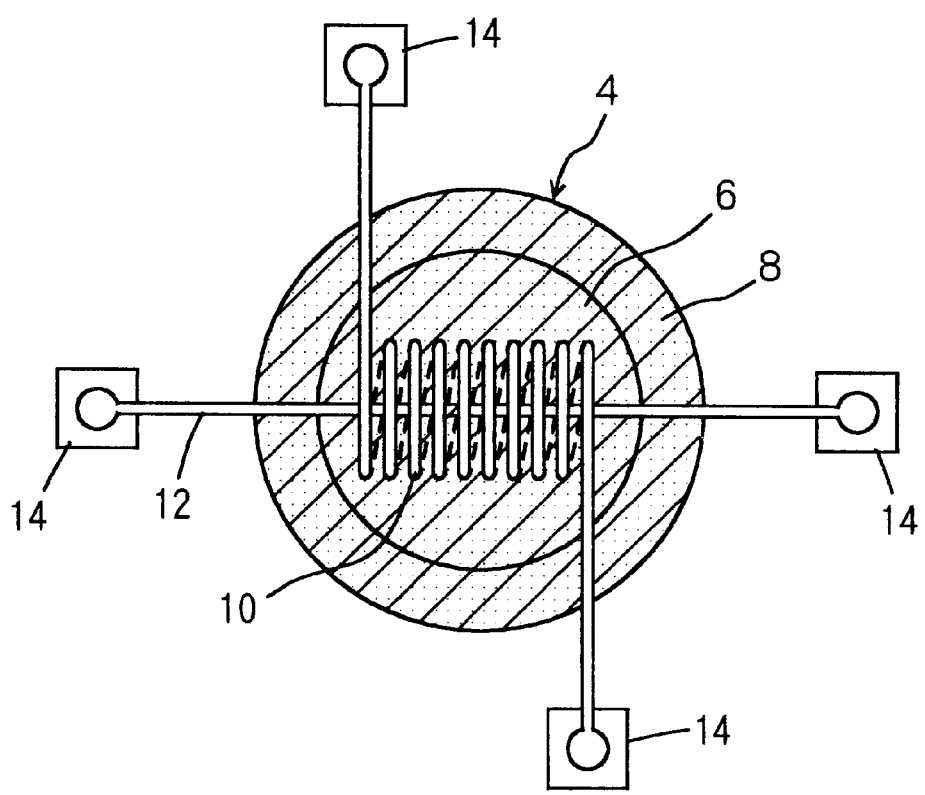
FIG. 1 is a sectional view of a gas sensor of an embodiment.

FIG. 1 through FIG. 9 show an embodiment. FIG. 1 shows the structure of a gas sensor 2, and 4 denotes a metal oxide semiconductor bead, which has a two-layer structure of an inner area 6 and a filter 8. The inner area 6 is provided in such a way that it completely covers a coil of a heater electrode 10 that will be described below. The main component of the inner area 6 is $SnO_2$, to which a precious metal catalyst, such as Pd, is added. The inner area 6 is a sintered body of the oxide, to which an aggregate, such as α-alumina, is mixed if it is desired. The addition of α-alumina to one hundred parts by weight of $SnO_2$ is, for example, from zero to fifty parts by weight. Ten parts by weight of α-alumina are added herein. The filter 8 was provided in such a way that it completely covered the inner area 6. Like the inner area 6, the filter 8 is a sintered body of a mixture of $SnO_2$ with the added precious metal catalyst and an aggregate, such as α-alumina.

The material for the filter 8 differs from that of the inner area 6. Generally speaking, the aggregate content (in weight %) of the filter 8 is equal to or higher than that of the inner area 6, and the inner area 6 may not contain any aggregate. The aggregate for the inner area 6 and for the filter 8 is not limited to α-alumina. Silica and zeolite will do, and different kinds of aggregate may be used for the inner area 6 and for the filter 8, respectively. Pd was used as the catalyst herein, but other precious metals, such as Pt, may be used and different precious metal catalysts may be used for the inner area 6 and for the filter 8, respectively. For example, the concentration, by weight, of the precious metal catalyst in conversion to metal (concentration in proportion to the total of the aggregate and $SnO_2$) is made lower in the filter 8 than in the inner area 6.

Reference numeral 10 denotes a heater electrode. It is coiled and its wire diameter is from 10 to 25 μm. Pt wire of 20 μm in diameter is used herein. The wire material for the heater electrode 10 is not limited to Pt; it is desirable to use Pt-based alloys of high resistance, such as Pt—W, Pt—Mo, Pt—Ti, Pt—Ni, Pt—Cr, Pt—Fe, Pt—Al and PT—ZGS. The number of turns of the coil of the heater electrode 10 is, for example, from three to thirteen, and ten turns are used herein. The inside diameter of the coil is set, for example, at 150 μm, and the coil length is set, for example, at 300 μm. Both ends of the heater electrode 10 are fixed to stems 14.

Reference numeral 12 denotes a central electrode, and like the heater electrode 10, it is made of Pt wire. The wire diameter is desirably from 10 to 25 μm, and it is set at 20 μm herein. Like the heater electrode 10, the wire material for the central electrode 12 is not limited to Pt; it is desirable to use Pt-based alloys of high resistance, such as Pt—W, Pt—Mo, Pt—Ti, Pt—Ni, Pt—Cr, Pt—Fe, Pt—Al, and Pt—ZGS. The central electrode 12 is arranged along the center line of the coil of the heater electrode 10, and both ends of the central electrode 12 are fixed to stems 14. The central electrode 12 may not be provided. In that case, gas detection is made by using a fact that the resistances of the heater electrode 10 and the bead 4, which are connected in parallel, change according to the condition of a gas.

The bead 4 is ellipsoidal or spherical. When it is spherical, its diameter is from 300 μm to 510 μm, and preferably from 380 μm to 490 μm, and its total volume is from $15\times10^{-3}$ $mm^3$ to $70\times10^{-3}$ $mm^3$, and preferably from $30\times10^{-3}$ $mm^3$. The inner area 6 is also ellipsoidal or spherical. When it is spherical, its diameter is from 120 μm to 320 μm, preferably from 180 μm to 270 μm, and more preferably from 200 μm to 250 μm. The volume of the inner area 6 is from $1\times10^{-3}$ $mm^3$ to $16\times10^{-3}$ $mm^3$, preferably from $3\times10^{-3}$ $mm^3$ to $10\times10^{-3}$ $mm^3$, and more preferably from $4\times10^{-3}$ $mm^3$ to $10\times10^{-3}$ $mm^3$. The ratio of the total volume of the bead 4 to the volume of the inner area 6 is from four to twenty, preferably from four to fifteen, and more preferably from five to fifteen.

It is desirable to bring the sensor resistance Rs in methane and the sensor resistance Rs in CO closer to each other. The higher is the methane sensitivity, the better. The higher is the selectivity from hydrogen towards CO and methane, the better. The letter β denotes the dependency on the concentration of the gas to be detected. The letter β indicates the ratio of resistances after and before the concentration of methane or CO is increased by a certain range. It is desirable to decrease β in methane. In CO, it is desirable to increase β at low concentration (from 100 ppm to 300 ppm).

The high temperature characteristics of the gas sensor 2 is determined mainly by the total volume of the bead 4. The methane sensitivity, selectivity from $H_2$ and dependency on methane concentration of the sensor 2 can be increased by reducing the total volume of the bead 4.

The low temperature characteristics of the gas sensor 2 depend on the volume of the inner area 6 and the ratio of the total volume to the volume of the inner area 6. By reducing the volume of the inner area 6, the sensor resistance Rs in CO can be reduced, the selectivity from $H_2$ can be improved, and the concentration dependency in CO of low concentrations can be reduced. By increasing the ratio of the total volume of the bead 4 to the volume of the inner area 6, the sensor resistance Rs in CO can be reduced, the selectivity from $H_2$ can be improved, and the concentration dependency in CO of low concentration can be reduced.

Figure 2:
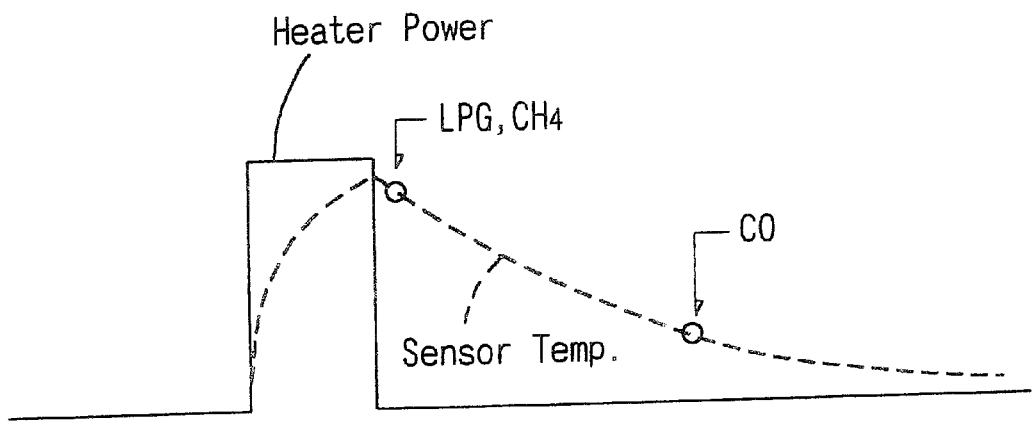
FIG. 2 is a characteristic diagram showing the operation pattern of the gas sensor of the embodiment.
Figure 3:
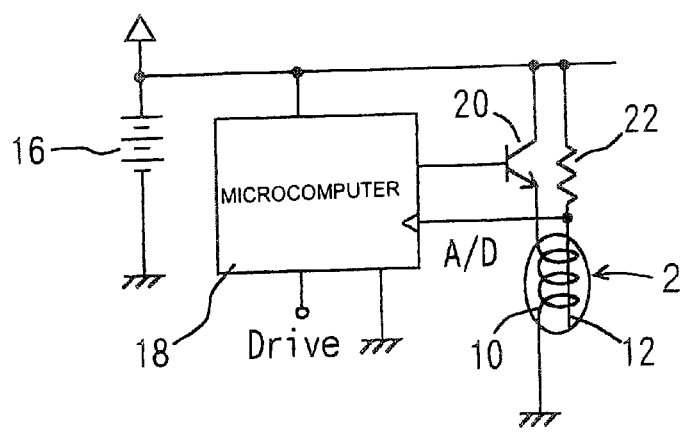
FIG. 3 is a block diagram of the driving circuit of the gas sensor of the embodiment.

FIG. 2 shows an example of driving pattern of the gas sensor 2, and FIG. 3 shows an example of the driving circuit of the gas sensor 2. The power source is, for example, a battery 16. Reference numeral 18 denotes a microcomputer for signal processing. Reference numeral 20 is a transistor, and 22 is a load resistance. The sensor signals are inputted through the A/D input of the microcomputer 18 to detect CO and a combustible gas, such as methane. The transistor 20 is driven by the microcomputer 18 to pulsatively turn on the heater through PWM control; the transistor 20 increases the duty ratio for turning on the heater at a high temperature and reduces the duty ratio at a low temperature. In the first three seconds of the 10-second cycle, the maximum temperature of the heater electrode 4 is, for example, from 400 to 600° C., and was set at 500° C. herein, which is suited to methane detection. At low temperature, the duty ratio of the heater electrode 4 is reduced to let it cool down; CO is detected at, for example, about 70° C.

Experimental Results

Gas sensors of nine different sizes were produced in the following manner. A heater electrode 10 of Pt wire of 20 μm in diameter was coiled; the inside diameter of the coil was 150 μm, the coil length was 300 μm, and the number of turns was ten. A central electrode 12 of Pt wire of 20 μm in diameter was provided at a center of the coil of the heater electrode 10. One part by weight of Pd was added to one hundred parts by weight of $SnO_2$. Then the one hundred parts by weight of $SnO_2$ after the addition of Pd where mixed with 10 parts by weight of α-alumina to prepare a paste of an appropriate consistency. The paste was applied onto the coil of the heater electrode 10 and dried to form an inner area 6. One-half part by weight of Pd was added to one hundred parts by weight of $SnO_2$, and the resulted $SnO_2$ was mixed with α-alumina at a ratio of 1:1 to prepare a paste of an appropriate consistency. The paste applied onto the inner area 6 and dried to form a filter 8, and the filter 8 was baked at from 650 to 700° C. In this way sensors, of which inner areas 6 are, in volume, 4, 4, 8, 8, 9, 14, 15, 24, and 29 (the unit is $10^{-3}$ mm$^3$), were produced on a trial basis.

The aggregate content and the precious metal catalyst concentration of the inner area 6 were lower than those of the filter 8. It was necessary for enhancing the CO sensitivity at low temperature and for ensuring selectivity from $H_2$ towards CO.

In addition to them, a gas sensor 2 was produced in the same manner with the above-mentioned sensors, except Pt wire of 15 μm in diameter was used for both the heater electrode 10 and the central electrode 12, and the heater electrode 10 was made into a coil, of which the inside diameter was 100 μm, the coil length was 100 μm, and the number of turns was five. In this way a sensor, of which the inner area 6 was 4×10$^{-3}$ mm$^3$ in volume, was produced on a trial basis.

The inner area 6 was spherical or ellipsoidal; the major axis was from 200 to 400 μm and the minor axis was from 200 to 400 μm. As for the volume of the inner area, there were nine kinds; 4, 4, 8, 8, 9, 14, 15, 24 and 29 (the unit is $10^{-3}$ mm$^3$). The bead 4 was spherical or ellipsoidal; the major axis was from 380 to 650 μm and the minor axis was from 380 to 550 μm. The total volumes of the above-mentioned sensors of nine kinds were 30, 50, 40, 93, 79, 100, 58, 78, and 69 (the unit is $10^{-3}$ mm$^3$), respectively. The ratios of the total volume of the bead 4 to the volume of the inner area 6 of the above-mentioned sensors of nine kinds were eight, thirteen, five, twelve, nine, seven, four, three, and two, respectively.

The gas sensor 2 was driven, as shown in FIG. 2, and the sensor resistances Rs at high temperature, 500° C., in methane, air, and hydrogen were measured. Similarly, the sensor resistances Rs at the low temperature near the room temperature, in CO and hydrogen were measured. The methane concentration was from 1000 to 3000 ppm and the CO concentration was from 100 to 1000 ppm. From these measurements, the methane sensitivity (the ratio of the sensor resistance in air to that in methane of 3000 ppm), selectivity from $H_2$ (the ratio of the sensor resistance in $H_2$ of 1000 ppm to that in methane of 3000 ppm or in CO of 100 ppm), methane concentration dependency β (the ratio of the sensor resistance in methane of 3000 ppm to that in methane of 1000 ppm) and CO concentration dependency β (the ratio of the sensor resistance in CO of 1000 ppm to that in CO of 300 ppm, and the ratio of the sensor resistance in CO of 300 ppm to that in CO of 100 ppm) were obtained. A total of twenty sample sensors were used for each kind of the sensor in the experiment.

FIG. 4 through FIG. 9 show the results in terms of the mean values of the twenty sample sensors for each kind. The methane sensitivity is the ratio of the sensor resistance Rs in air to the sensor resistance Rs in methane, and the selectivity from $H_2$ at high temperature is the ratio of the sensor resistance in hydrogen of 1000 ppm to that in methane of 3000 ppm. The concentration dependency β (1000–3000) is the ratio of the resistance in methane of 3000 ppm to that in methane of 1000 ppm. The concentration dependency β (1000–3000) is the ratio of the resistance in methane of 3000 ppm to that in methane of 1000 ppm. The concentration dependency β (300–1000) is the ratio of the resistance in CO of 1000 ppm to that in CO of 300 ppm. β (100–300) is the ratio of the resistance in CO of 300 ppm to that in CO of 100 ppm.

Figure 4:
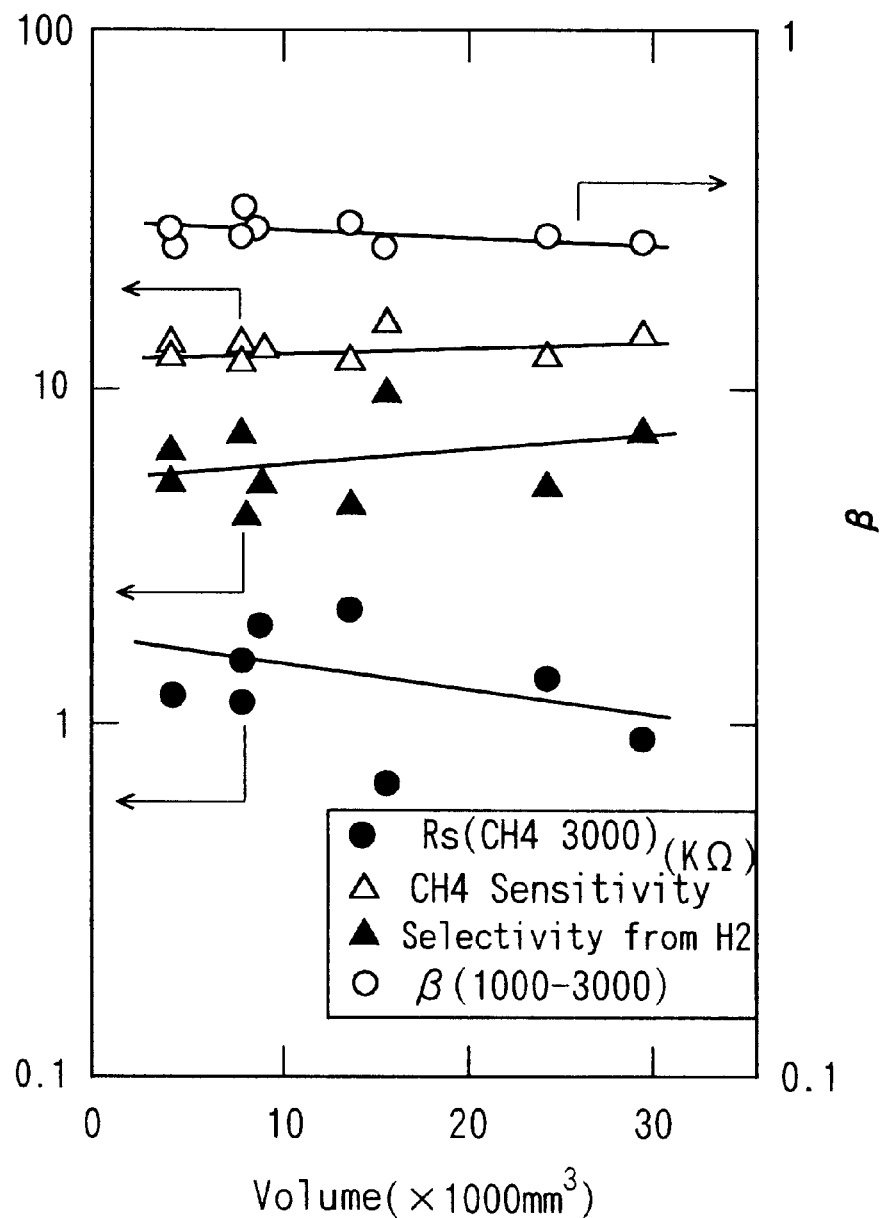
FIG. 4 is a characteristic diagram showing the relationship between the inner volume and the sensor characteristics at high temperature of the gas senor.

FIG. 4 and FIG. 5 show the relationships between the volume of the inner area 6 and the sensor characteristics. At high temperature, as shown in FIG. 4, even when the volume of the inner area 6 was changed, the sensor resistance Rs in methane, $CH_4$, sensitivity, selectivity from $H_2$, and concentration dependency β did not change much. At low temperature, as shown in FIG. 5, when the volume of the inner area 6 was reduced, the sensor resistance Rs in CO was lowered, the selectivity from $H_2$ was improved, and the concentration dependency β at low concentration was increased, respectively.

Figure 6:
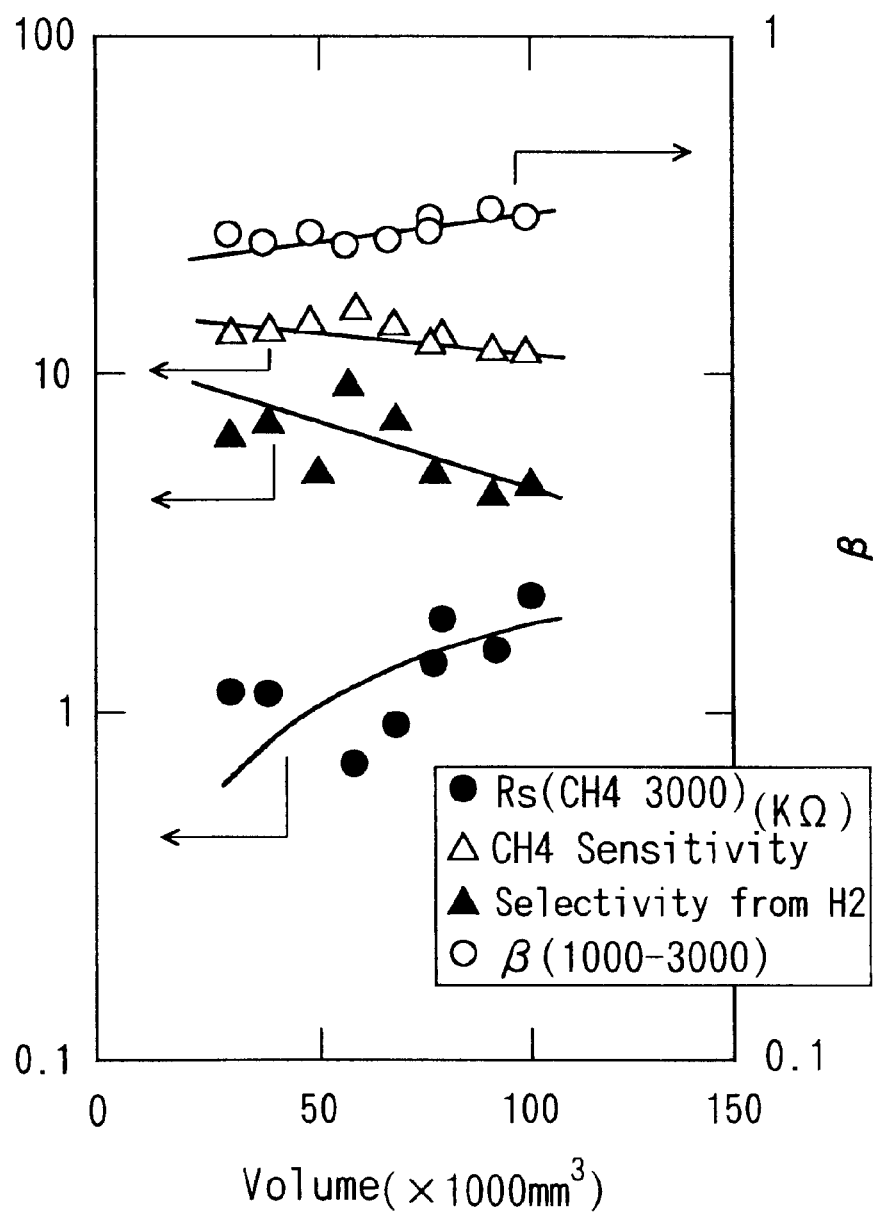
FIG. 6 is a characteristic diagram showing the relationship between the bead total volume and the sensor characteristics at high temperature of the gas sensor.
Figure 7:
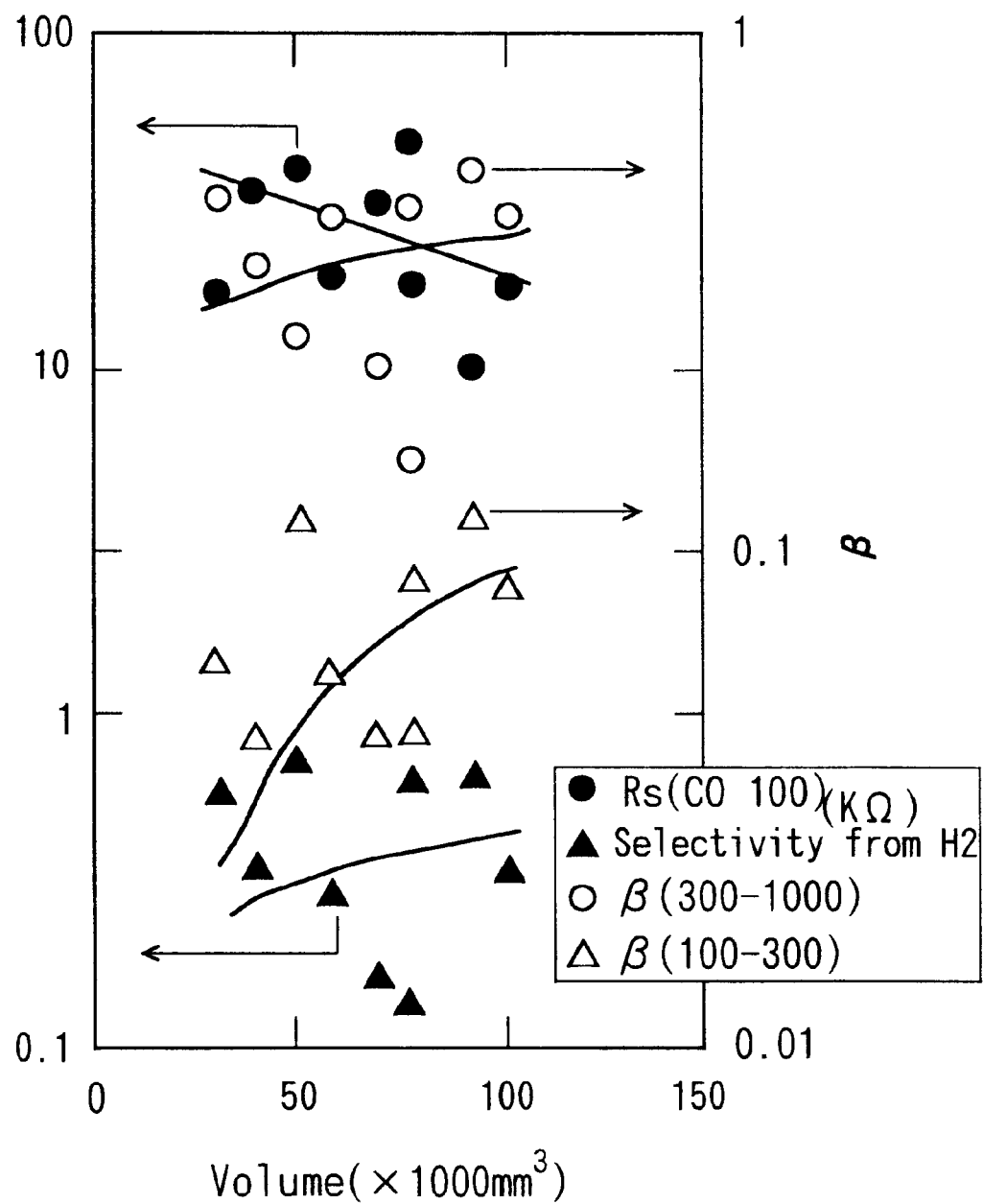
FIG. 7 is a characteristic diagram showing the relationship between the bead total volume and the sensor characteristics at low temperature of the gas sensor.

FIG. 6 and FIG. 7 show the relationships between the total volume of the bead 4 and the sensor characteristics. At high temperature, as shown in FIG. 6, when the total volume was reduced, the $CH_4$ sensitivity was improved, the selectivity from $H_2$ was increased, and the value of the concentration dependency β was reduced. At low temperature, as shown in FIG. 7, the correlations between the total volume of the bead 4 and the sensor resistance Rs in CO, selectivity from $H_2$, and concentration dependency β were low.

Figure 8:
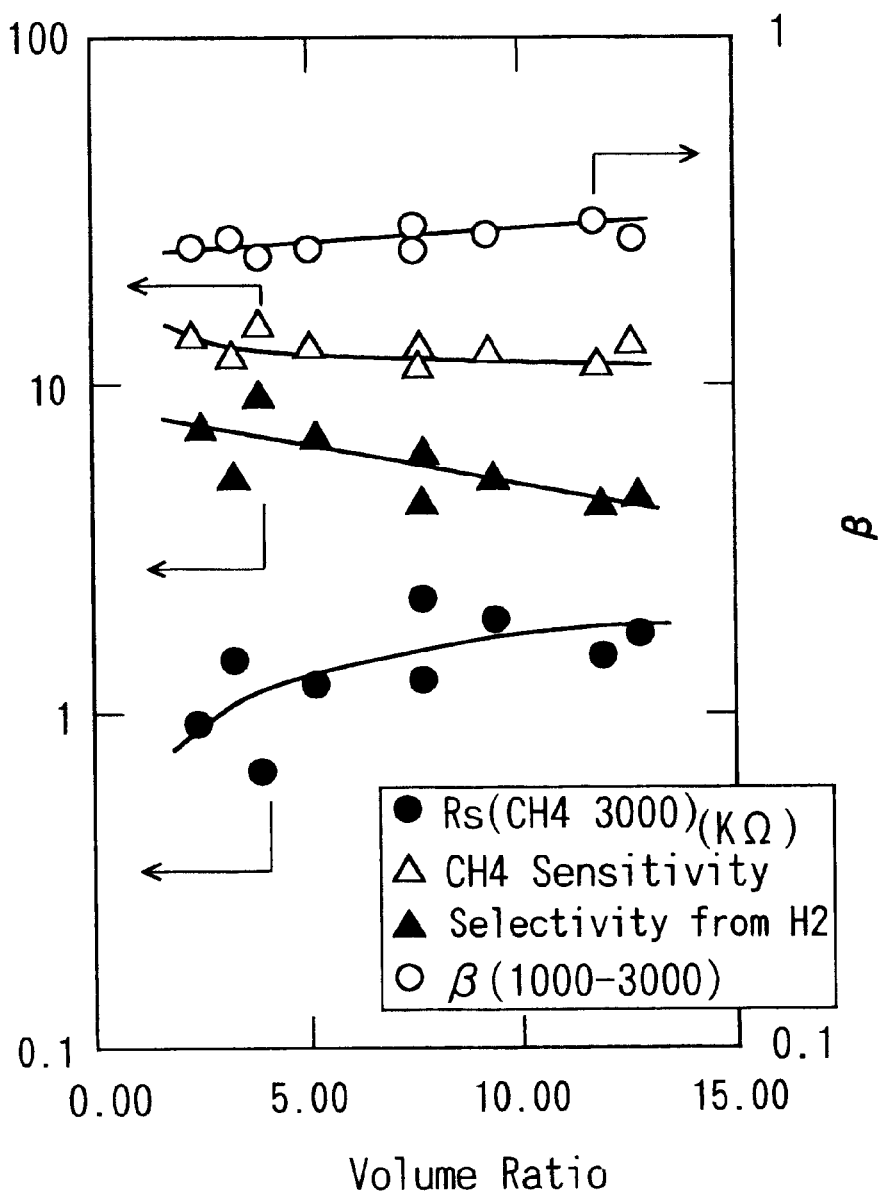
FIG. 8 is a characteristic diagram showing the relationship between the ratio of the bead total volume to the inner volume and the sensor characteristics at high temperature of the gas sensor.
Figure 9:
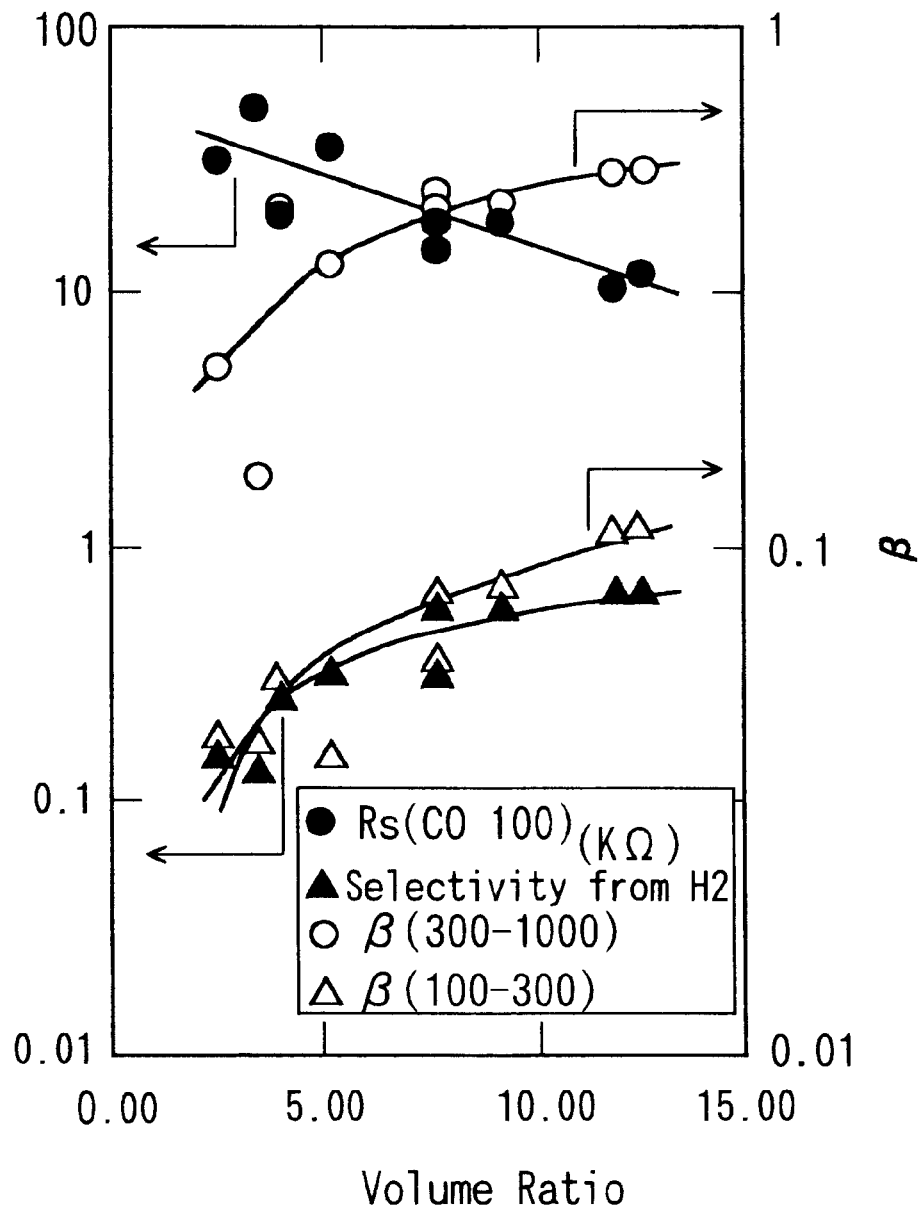
FIG. 9 is a characteristic diagram showing the relationship between the ratio of the bead total volume to the inner volume and the sensor characteristics at low temperature of the gas sensor.

FIG. 8 and FIG. 9 show the influences of the ratio of the total volume of the bead 4 to the volume of the inner area 6 on the sensor characteristics. At high temperature, as shown in FIG. 8, even when the ratio was changed, the sensor resistance Rs in methane, $CH_4$ sensitivity, selectivity from $H_2$, and concentration dependency β did not change much. At low temperature, as shown in FIG. 9, the sensor resistance Rs exhibited a high dependency on volume ratio. When the ratio was increased, the sensor resistance Rs in CO was lowered, the selectivity from $H_2$ was improved, and the concentration dependency β at low concentration was increased, respectively.

From the view points of drop resistance and impact strength of the gas sensor 2, the smaller is the total volume of the bead 4, the better. When the volume of the bead 4 is reduced, the power consumption of the gas sensor 2 will be reduced. On the other hand, it is difficult in production to extremely reduce the volume of the inner area 6. On the basis of these points, the volume of the inner area 6 is set at from 1×10$^{-3}$ mm$^3$ to 16×10$^{-3}$ mm$^3$, preferably from 3×10$^{-3}$ mm$^3$ to 10×10$^{-3}$ mm$^3$, and more preferably from 4×10$^{-3}$ mm$^3$ to 10×10$^{-3}$ mm$^3$. The total volume of the bead 4 including both the inner area 6 and the filter 8 is from 15×10$^{-3}$ mm$^3$ to 70×10$^{-3}$ mm$^3$, and preferably from 30×10$^{-3}$ mm$^3$ to 60×10$^{-3}$ mm$^3$. The ratio of the total volume of the bead 4 to that of the inner area 6 is from four to twenty, preferably from four to fifteen, and more preferably from five to fifteen.

What is claimed is:

1. A gas sensor wherein an inner area of $SnO_2$ is provided to cover a coiled heater electrode and the inner area is covered by a filter, said gas sensor being characterized in that the volume of the inner area is from 1×10$^{-3}$ mm$^3$ to 16×10$^{-3}$ mm$^3$, and [p<]bold1 that the ratio of the total volume of the inner area and the filter to the volume of the inner area is from four to twenty.

2. A gas sensor of claim 1 characterized in that the volume of the inner area is from 3×10$^{-3}$ mm$^3$ to 10×10$^{-3}$ mm$^3$, the ratio of the total volume of the inner area and the filter to the volume of the inner area is from four to fifteen, and the total volume of the inner area and the filter is from 15×10$^{-3}$ mm$^3$ to 70×10$^{-3}$ mm$^3$.

3. A gas sensor of claim 2 characterized in that the volume of the inner area is from 4×10$^{-3}$ to 10×10$^{-3}$ mm$^3$, the ratio of the total volume of the inner area and the filter to the volume of the inner area is from five to fifteen, and the total volume of the inner area and the filter is from 30×10$^{-3}$ mm$^3$ to 60×10$^{-3}$ mm$^3$.

4. A gas sensor of claim 1 characterized in that a central electrode is provided at the center of the heater electrode.

5. A gas sensor of claim 1 characterized in that the filter contains an aggregate at a rate equal to or higher than that in the inner area.

6. A gas sensor of claim 1 characterized in that both the filter and the inner area contain at least a precious metal catalyst and that the precious metal concentration in the filter is lower than the precious metal concentration in the inner area.

* * * * *